US006544977B1

United States Patent
Godard et al.

(10) Patent No.: US 6,544,977 B1
(45) Date of Patent: *Apr. 8, 2003

(54) **CRYSTALLINE FORMS OF 1S-[1-ALPHA(2S*, 3R*), 9ALPHA]6, 10-DIOXO-N-(2-ETHOXY-5-OXO-TETRAHYDRO-3-FURANYL)-9[[(1-ISOQUINOLYL)CARBONYL]AMINO] OCTAHYDRO-6H-PYRIDAZINO [1,2-A] [1,2] DIAZEPIN-1-CARBOXAMIDE**

(75) Inventors: Jean-Yves Godard, Le Raincy (FR); Valerie Rognon, Coubron (FR)

(73) Assignee: Aventis Pharma S.A. (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/647,858
(22) PCT Filed: Apr. 7, 1999
(86) PCT No.: PCT/FR99/00799
§ 371 (c)(1), (2), (4) Date: Nov. 20, 2000
(87) PCT Pub. No.: WO99/52935
PCT Pub. Date: Oct. 21, 1999

(30) Foreign Application Priority Data

Apr. 8, 1998 (FR) .............................................. 98 04367

(51) Int. Cl.$^7$ ...................... C07D 243/02; A61K 31/551
(52) U.S. Cl. ................................. 514/211.05; 540/460
(58) Field of Search ....................... 514/211.05; 540/460

(56) References Cited

U.S. PATENT DOCUMENTS 6,258,948 B1 * 7/2001 Batchelor et al. ........... 540/500

FOREIGN PATENT DOCUMENTS

WO           9722619           6/1997

OTHER PUBLICATIONS

Streitwieser, A. and Heathcock, C.H., "Introduction to Organic Chemistry, 2nd Ed.", Macmillan, New York, 1981, p. 127–131.*
Chemical Abstracts name and strucure for RN [192755-52-5].*
Pauling, Linus, "General Chemistry, 2nd Ed.", 1953, Freeman, San Francisco, p22 & 41.*
Loewenthal, H.J.E., "A Guide for the Perplexed Organic Experimentalist" 2$^{nd}$ Ed., John Wiley, New York, 1990, pp. 145–146.*

* cited by examiner

Primary Examiner—Richard L. Raymond
Assistant Examiner—Thomas McKenzie
(74) Attorney, Agent, or Firm—Bierman, Muserlian and Lucas

(57) ABSTRACT

Two new crystalline forms of 1S-[1alpha(2S*,3R*), 9alpha] 6,10-dioxo-N-(2-ethoxy-5-oxo-tetrahydro-3-furanyl)-9 [[(1-isoquiinolyl)carbonyl]amino]octahydro-6H-pyridazino[1,2-a][1,2]diazepin-1-carboxamide (anhydrous or hydrated), their preparation process and the pharmaceutical compositions containing them.

7 Claims, 6 Drawing Sheets

CRYSTALLINE FORMS OF 1S-[1-ALPHA(2S*, 3R*), 9ALPHA]6, 10-DIOXO-N-(2-ETHOXY-5-OXO-TETRAHYDRO-3-FURANYL)-9[[(1-ISOQUINOLYL)CARBONYL]AMINO] OCTAHYDRO-6H-PYRIDAZINO [1,2-A] [1,2] DIAZEPIN-1-CARBOXAMIDE

This application is a 371 of PCT/FR99/00799 filed Apr. 7, 1999.

A subject of the present invention is two new crystalline forms of 1S-[1alpha(2S*,3R*),9alpha]6,10-dioxo-N-(2-ethoxy-5-oxo-tetrahydro-3-furanyl)-9[[(1-isoquinolyl)carbonyl]amino]octahydro-6H-pyridazino[1,2-a][1,2]diazepin-1-carboxamide (anhydrous or hydrated), their preparation process and the pharmaceutical compositions containing them.

Patent Application WO 9722619 describes 1S-[1-alpha(2S*,3R*) 9alpha]6,10-dioxo-N-(2-ethoxy-5-oxo-tetrahydro-3-furanyl)-9[[(1-isoquinolyl)carbonyl]amino]octahydro-6H-pyridazino[1,2-a][1,2-]diazepin-1-carboxamide as well as its pharmaceutically acceptable salts (product 412f: Compound I) as inhibitors of the interleukin-1beta conversion enzyme:

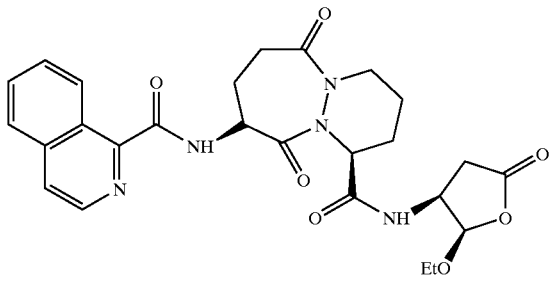

Compound (I) as described and prepared in this Application WO9722619 is found in amorphous form. It mainly has the drawback of being hygroscopic.

The preparation of compound (I) is carried out in the following way: Amidification reaction between (1S,9S)9-(isoquinolin-1-oylamino)-6,10-dioxo-1,2,3,4,7,8,9,10-octahydro-6H-pyridazino-[1,2-a][1,2]-diazepin-1-carboxylic acid and (3S,2S)3-allyloxycarbonylamino-2-benzyloxy-5-oxotetrahydrofuran in the presence of dimethylbarbituric acid, tetrakistriphenylphosphine palladium, 1-hydroxybenzotriazole and 1(3-dimethylaminopropyl)-3-ethylcarbodiimide hydrochloride in methylene chloride, dimethylformamide or a mixture of these two solvents. The product is purified by chromatography (Ethyl acetate/dichloromethane) in order to produce amorphous compound (I).

OBJECT OF THE INVENTION

A subject of the invention is to find one or more new crystalline forms which do not have the drawbacks of the amorphous form.

THE INVENTION

The solid forms, and in particular the pharmaceutical products, can have more than one crystalline form. This is what is called polymorphism.

The polymorphous forms of the same molecule in general show different physical properties such as solubility, hygroscopicity and stability. It should be noted that for the moment methods do not exist which allow the existence of such-and-such a polymorph, nor their physical properties to be predicted.

Obtaining new polymorphous forms of molecules having a therapeutic activity is of great interest to the pharmaceutical industry in particular from the point of view of their preparation on an industrial scale, their use in pharmaceutical compositions, the search for better stability and better bioavailabilty. (Byrn, S. R., Solid-State Chemistry of Drugs, New York, Academ. Press (1982); Kuhnert-Brandstatter, M, Thermomicroscopy In the Analysis of Pharmaceuticals, New York, Pergamon Press (1971); J. Halebian et al. J. Pharm. Science (1969) vol 58(8) 911; J. Halebian et al. J. Pharm. Science (1975) vol 64(8) 1269–1288).

By polymorphous form is meant all asolvated forms of a crystallized molecule, and by pseudo-polymorphous form all solvated forms.

The methods for analyzing the crystalline forms are as follows:

Thermal behaviour: it is determined by DSC (differential scanning calorimetry): 2 to 5 mg of the substance to be studied is weighed into a non-hermetically sealed aluminium capsule. The analysis is carried out, accompanied by flushing with nitrogen, from 25 to 350° C. at a rate of temperature rise of 20° C./mn.

IR (Infrared): The substance to be studied is dispersed in liquid paraffin oil. The analysis is carried out on a Fourier transform infrared (FTIR) spectrophotometer from 4000 to 600 cm$^{-1}$.

XR (powder X-ray diffraction): The substance to be studied is distributed in the compartment of a glass sample holder. The analysis is carried out by scanning from 2° to 38° (2 theta) with a step of 0.02° and counting for 1 second per step. The X-ray source is a Cuivre tube (45 kV, 30 mA).

The Applicant has revealed two new crystalline forms (form A and form B). Form A which is anhydrous and form B which is hydrated. The crystalline form A has, in addition to the advantages mentioned above, an absence of hygroscopicity (see the test below).

Therefore, firstly a subject of the invention is a new crystalline form of anhydrous 1S-[1alpha(2S*,3R*), 9alpha]6,10-dioxo-N-(2-ethoxy-5-oxo-tetrahydro-3-furanyl)-9[[(1-isoquinolyl)carbonyl]amino]octahydro-6H-pyridazino[1,2-a][1,2]diazepin-1-carboxamide which is called form A.

This form A has the following characteristics:

Crystalline system: triclinic a (Å): 8.02; b (Å): 9.21; c (Å) 17.70; alpha (degree): 91.38; beta (degree): 93.62; gamma (degree): 90.43; space group P1; Z 2.

A subject of the invention is also a new crystalline form of hydrated 1S-[1alpha(2S*,3R*),9alpha]6,10-dioxo-N-(2-ethoxy-5-oxo-tetrahydro-3-furanyl)-9[[(1-isoquinolyl)carbonyl]amino]octrahydro-6H-pyridazino[1,2-a][1,2]diazepin-1-carboxamide which is called form B.

Figure 1:
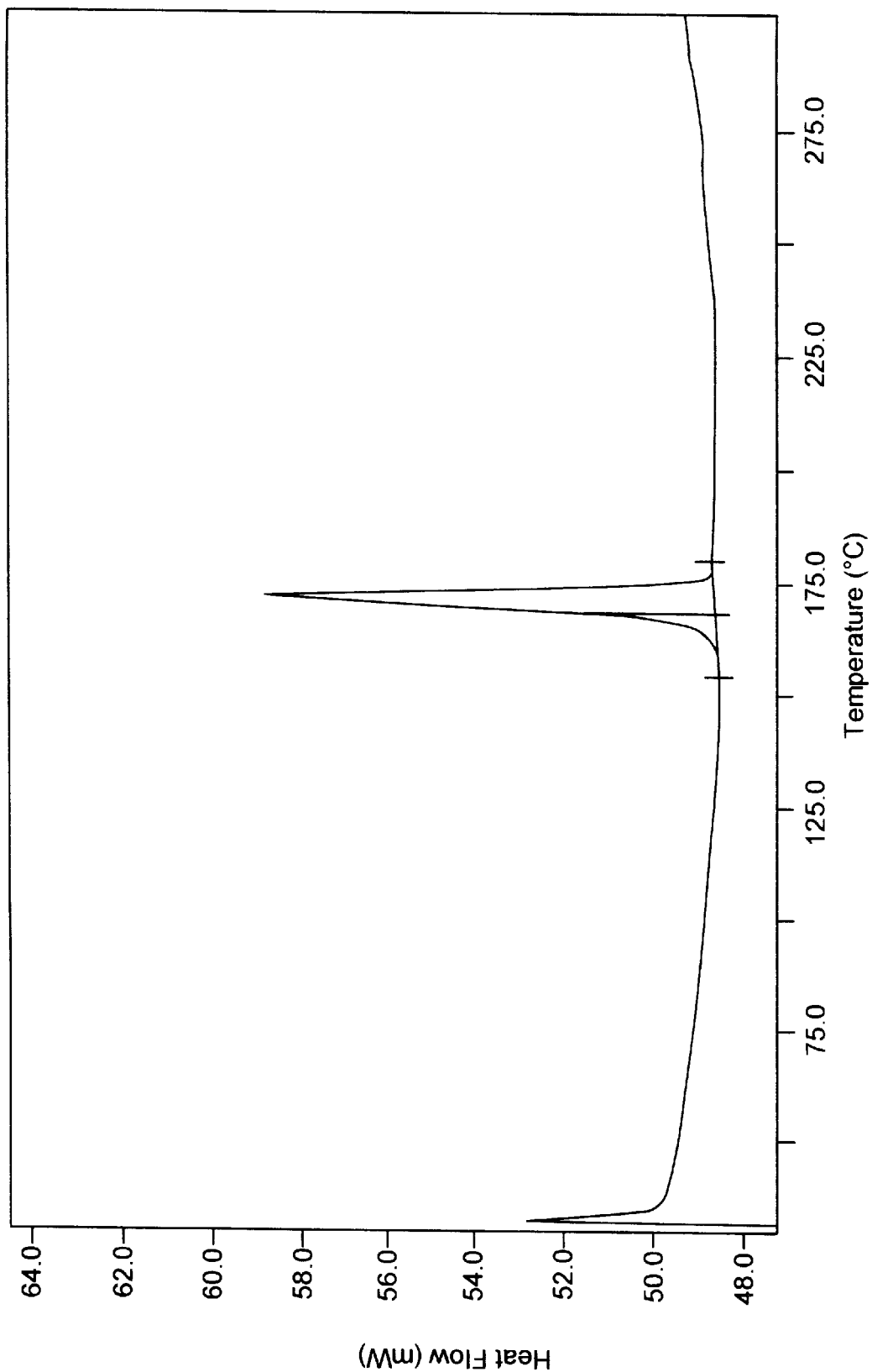
FIGS. 1 and 4 are the DCA graph for the compound of form A and B, respectively.

Form A has the following characteristics:

The anhydrous compound of formula (I), as prepared by one of the methods indicated below, has a specific crystalline form (form A). The physical characteristics are described in FIGS. 1A (DSC) 2A (IR) and 3A (XR).

DSC: Endothermal melting point from 168° C.

IR (nujol, cm$^{-1}$): 3253; 1789; 1702; 1681; 1644

XR (d,Å): 17.73; 8.87; 8.11; 7.50; 7.17; 6.31; 6.09; 5.81.

Form B has the following characteristics:

The hydrated compound of formula (I), as prepared by one of the methods indicated below, has a specific crystalline form (form B). The physical characteristics are described in FIGS. 1B (DSC) 2B (IR) and 3B (XR).

DSC: Endothermal dehydration between 50 and 110° C. and between 110 and 130° C. An endothermal melting point from 162° C. is observed.

IR (nujol, cm$^{-1}$): 3569; 3447; 3322; 1778; 1682; 1660

XR (d,Å): 11.34; 10.80; 10.06; 7.59; 7.16; 6.71; 6.41; 6.11; 5.44.

Therefore a subject of the invention is form A as defined previously having at least one of the following characteristics and preferably all the following characteristics:

a) Endothermal melting point from 168° C., b) infrared spectrum having characteristic absorptions at approximately (nujol, cm$^{-1}$): 3253; 1789; 1702; 1681; 1644, c) XR diffraction pattern having characteristic interlattice spacings equal to (d,Å): 17.73; 8.87; 8.11; 7.50; 7.17; 6.31; 6.09; 5.81.

Figure 2:
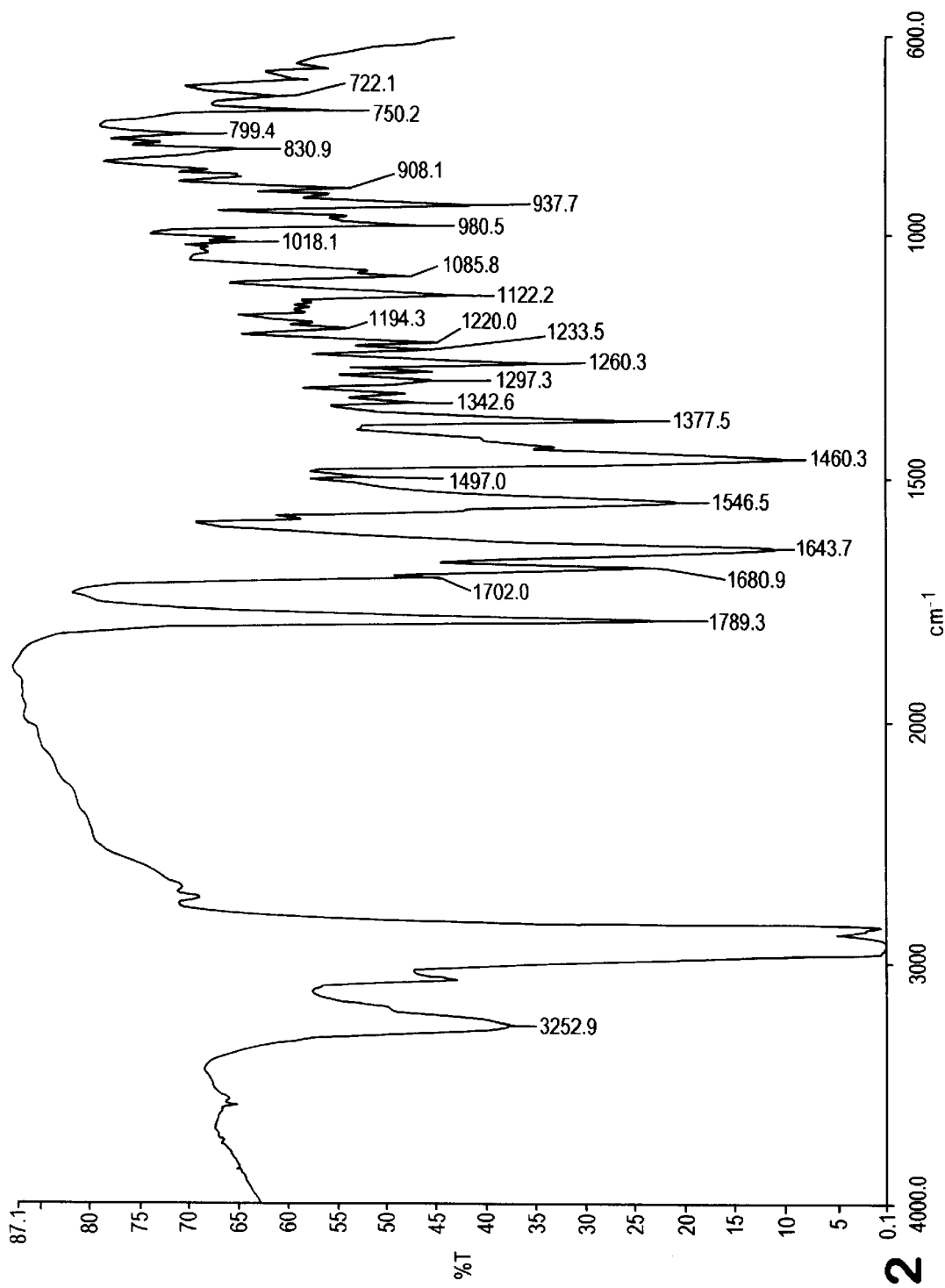
FIGS. 2 and 5 are the infrared graphs of the compound of form A and B, respectively.
Figure 3:
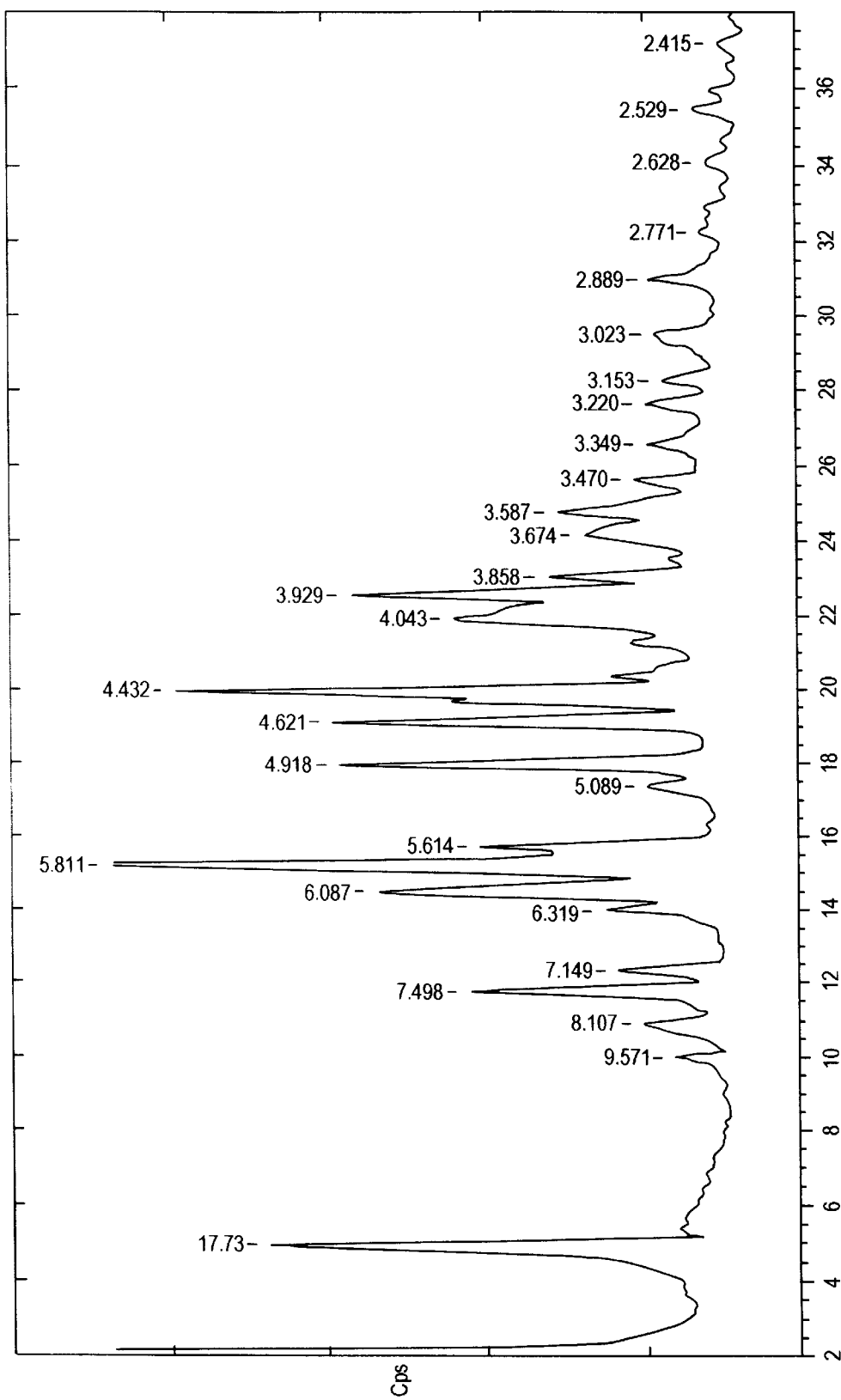
FIGS. 3 and 6 are the X-ray diffraction patterns for the compound of form A and B, respectively.
Figure 4:
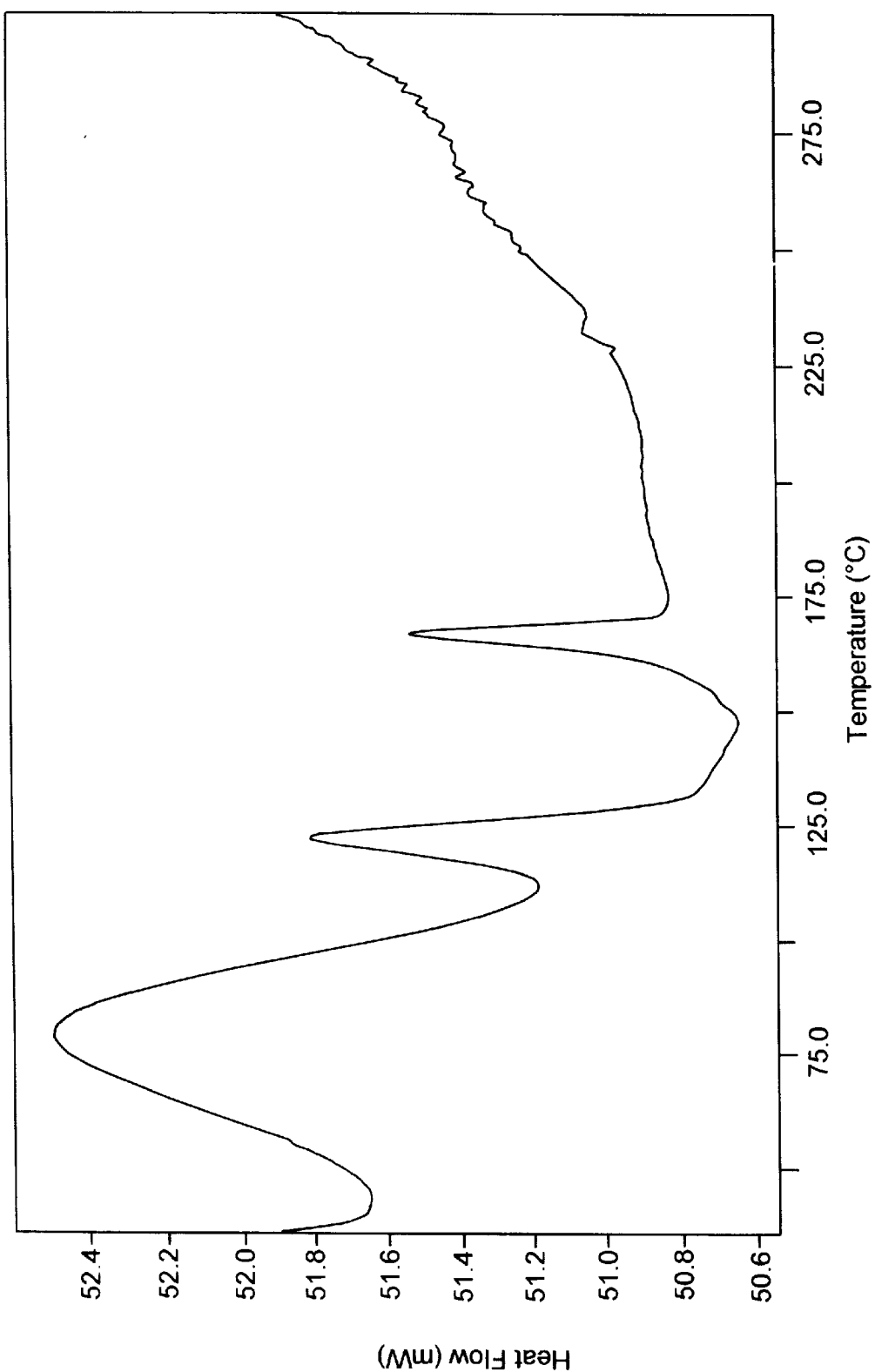
Figure 5:
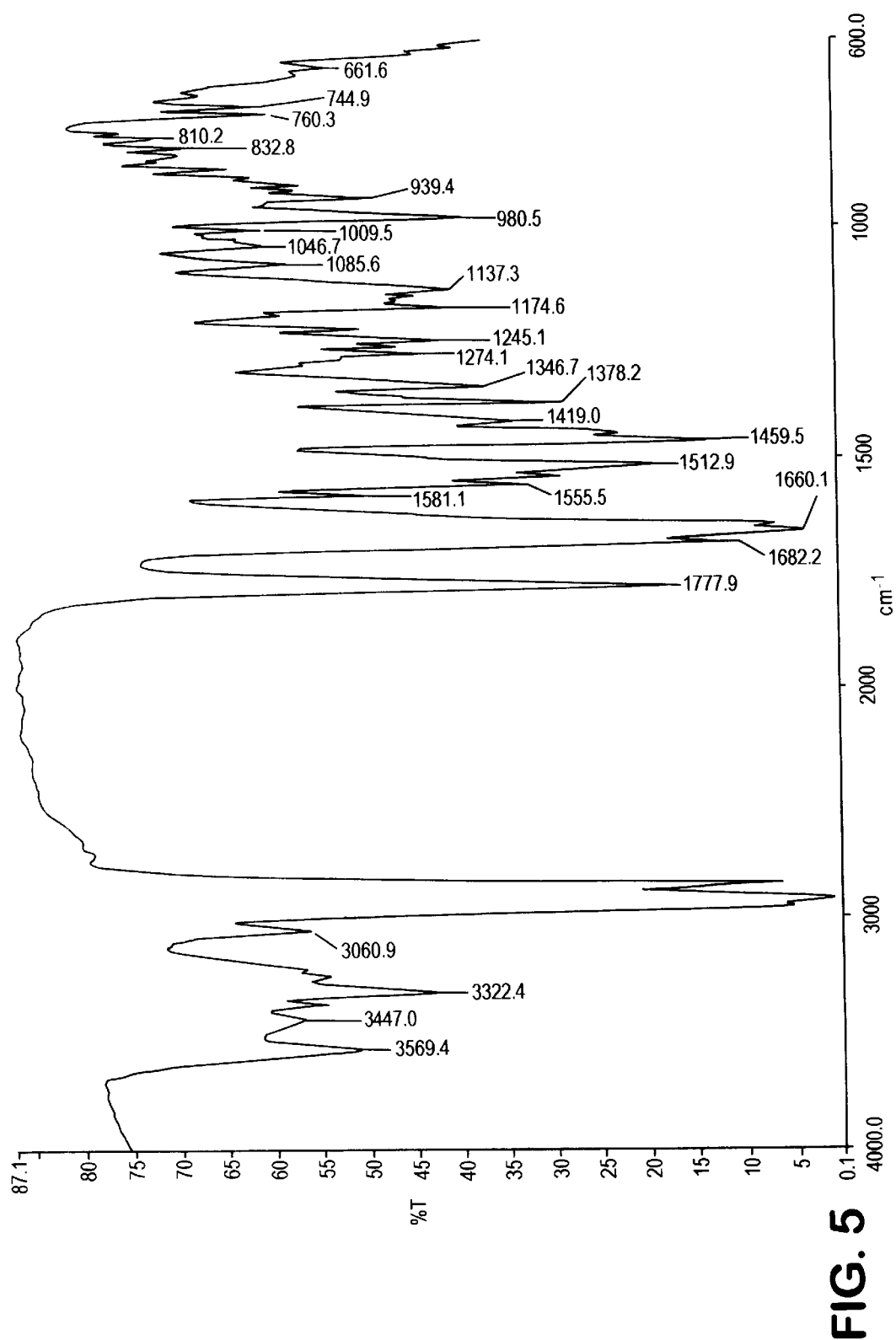
Figure 6:
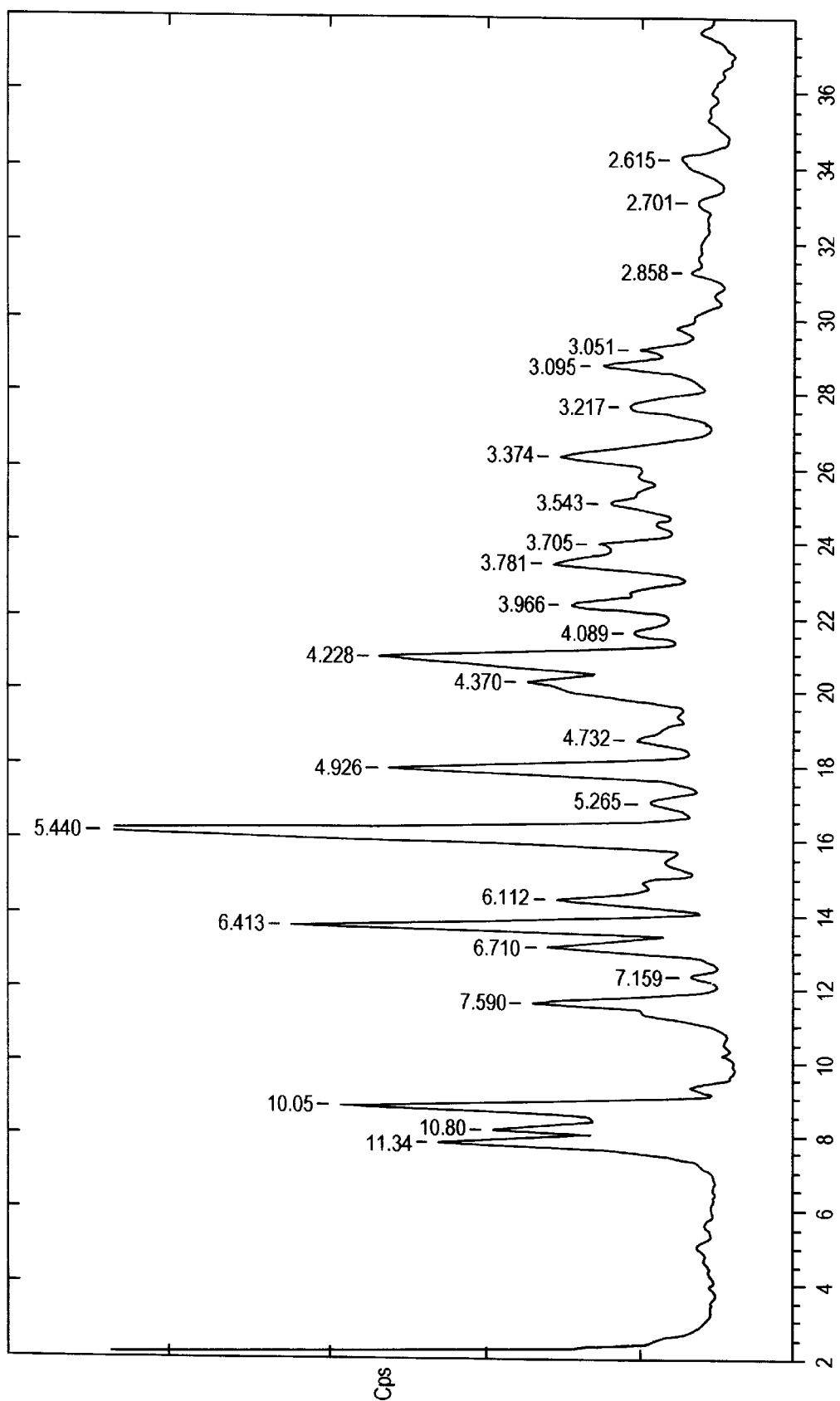

A more particular subject of the invention is form A as defined previously having an infrared spectrum substantially identical to that of FIG. 2A and an X-ray diffraction pattern substantially identical to that of FIG. 3A.

A subject of the invention is also form B as defined previously having at least one of the following characteristics and preferably all these following characteristics:

a) Endothermal dehydration between 50 and 110° C. and between 110 and 130° C. and an endothermal melting point from 162° C., b) infrared spectrum of form B having characteristic absorptions at approximately (nujol, cm$^{-1}$): 3569; 3447; 3322; 1778; 1682; 1660, c) XR diffraction pattern of form B having characteristic interlattice spacings equal to (d,Å): 11.34; 10.80; 10.06; 7.59; 7.16; 6.71; 6.41; 6.11; 5.44.

A more particular subject of the invention is also form B as defined previously having an infrared spectrum substantially identical to that of FIG. 2B and an XR diffraction pattern substantially identical to that of FIG. 3B.

A subject of the present invention is also a process for the preparation of form A or B, characterized in that the amorphous compound (I) obtained according to the method defined above is dissolved in an organic solvent or a mixture of these solvents, and in particular at ambient temperature, and after crystallization the expected form A or B is obtained.

Form A is preferably obtained by crystallization from an alcohol or an ether and in particular isopropyl ether, butanol or isopropanol.

Form A is also obtained by crystallization from a mixture of these solvents, in particular from an ethanol/isopropyl ether mixture.

Form B is quite particularly obtained by crystallization from toluene.

Obtaining the expected forms A or B can be, if appropriate, initiated by seeding the solution with a few crystals of form A or B respectively.

Isolation of forms A or B is carried out according to methods known to a person skilled in the art.

The crystalline forms A or B of the compound of formula (I) have the same therapeutic activities as those described for amorphous compound (I) in the Application WO97/22169 and WO95/35308.

They have an inhibitory activity on ICE (interleukin-1beta conversion enzyme) and are particularly useful in the treatment of inflammatory, auto-immune and neurodegenerative diseases.

Therefore a subject of the invention is the crystalline forms A or B as described previously as a medicament.

The crystalline forms A or B of the compound of formula (I) can be used by oral, parenteral, topical route, by inhalation, or via implants. They can be prescribed in the form of plain or sugar-coated tablets, gelatin capsules, granules, suppositories, pessaries, injectable preparations, ointments, creams, gels, microspheres, implants, patches, which are prepared according to the usual methods.

The crystalline forms A or B of the compound of formula (I) can be mixed with excipients, diluents and all vehicles known to a person skilled in the art for the manufacture of pharmaceutical compositions. As examples of excipients usually used in these pharmaceutical compositions the following can be mentioned: talc, gum arabic, lactose, starch, magnesium stearate, cacao butter, aqueous or non-aqueous vehicles, fatty substances of animal or vegetable origin, paraffin derivatives, glycols, various wetting, dispersing or emulsifying agents, preservatives.

The invention therefore extends to the pharmaceutical compositions containing as active ingredient at least one of the crystalline forms A or B of the compound of formula (I) as defined above and one or more pharmaceutically acceptable excipients, diluents or supports.

A subject of the invention is also the use of the crystalline forms A or B of the compound of formula (I), as defined above for the preparation of a medicament intended to inhibit ICE (interleukin-1beta conversion enzyme) activity.

The following examples illustrate the invention without however limiting it.

EXAMPLE 1

Obtaining Form A by Crystallization from n-butanol 1.5 ml of n-butanol is added to 300 mg of amorphous compound I (obtained according to the method described in the Application WO9722619) and the reaction medium is agitated for 2 hours and 15 minutes. Crystallization of the product is observed, which product is separated and dried at 20° C. under 4 mbars. 160 mg of the anhydrous compound of formula (I) (form A) is obtained.

EXAMPLE 2

Obtaining Form A by Crystallization from Isopropanol 1.5 ml of isopropanol is added to 300 mg of amorphous compound I (obtained according to the method described in the Application WO9722619) and the reaction medium is agitated at ambient temperature for 16 hours. Crystallization of the product is observed, which product is separated and dried at 20° C. under 4 mbars. 166 mg of the anhydrous compound of formula (I) (form A) is obtained.

EXAMPLE 3

Obtaining Form B by Crystallization from Toluene 1.5 ml of toluene is added to 300 mg of amorphous compound I (obtained according to the method described in the Application WO9722619) and the reaction medium is agitated at ambient temperature for 16 hours. Crystallization of the product is observed, which product is separated and dried at 20° C. under 4 mbars. The hydrated compound of formula (I) (form B) is obtained.

EXAMPLE 4

Obtaining Form A by Crystallization from an Isopropyl Ether/ethanol Mixture 23.8 ml of absolute ethanol is added, under nitrogen and agitation, to 11.9 g of amorphous compound (I) and the suspension is heated to 60°±2° C. in order to obtain a solution. The solution is cooled down to 40°±2° C., the crystallization is initiated and the solution is maintained for 1 hour at this temperature. Then 119 ml of isopropyl ether is added over 15 minutes at 4°±2° C. and the reaction medium is maintained for 15 minutes at this temperature, followed by cooling down to 20°±2° C. over 15 minutes, maintaining for 1 hour under these conditions, then cooling down again to 0°, +5° C. over 15 minutes and maintaining for 2 hours. The reaction medium is separated, washed with isopropyl ether, dried under reduced pressure at 20° C. for 12 hours and 11.3 g of the anhydrous compound of formula (I) (form A) is obtained.

Hygroscopicity Curve (or Water Sorption Isotherm)

The water sorption isotherms were obtained using a Dynamic Vapor Sorption DVS 1 device (Surface Measurements System Ltd) at a constant temperature and under a more or less hydrated nitrogen atmosphere. The degree of relative humidity (RH) of the atmosphere was modified in stages. The passage from one stage to the next is carried out when the weight of the sample to be analyzed has reached a constant value.

|        | AMORPHOUS | | ANHYDROUS FORM A | | HYDRATED FORM B | |
|--------|-----------|------------|----------|------------|----------|------------|
| RH (%) | Sorption  | Desorption | Sorption | Desorption | Sorption | Desorption |
| 0.0    | 0.00      | −0.20      | 0.00     | 0.11       | 0.00     | −0.11      |
| 12.0   | 0.67      | 1.48       | 0.03     | 0.12       | 1.41     | 1.42       |
| 21.0   | 0.97      | 2.09       | 0.05     | 0.14       | 2.36     | 2.33       |
| 32.0   | 1.29      | 2.58       | 0.07     | 0.19       | 3.23     | 3.14       |
| 43.0   | 1.60      | 2.94       | 0.09     | 0.21       | 3.88     | 3.75       |
| 51.0   | 1.83      | 3.19       | 0.11     | 0.22       | 4.26     | 4.13       |
| 57.0   | 2.03      | 3.35       | 0.13     | 0.21       | 4.53     | 4.40       |
| 66.0   | 2.37      | 3.61       | 0.14     | 0.21       | 4.92     | 4.75       |
| 75.0   | 2.90      | 3.90       | 0.14     | 0.21       | 5.27     | 5.08       |
| 80.0   | 3.71      | 4.12       | 0.16     | 0.21       | 5.45     | 5.30       |
| 90.0   | 5.11      | 4.94       | 0.14     | 0.19       | 5.93     | 5.96       |
| 96.0   | 5.93      | 5.93       | 0.06     | 0.06       | 6.86     | 6.86       |

During the sorption cycle form A is not hygroscopic (<0.2%). The non-hygroscopicity was confirmed by leaving a sample for 7 days in a chamber at 96% relative humidity (at 32° C.). An absorption of water of approximately 0.15% was observed. The hydrated form (form B) is more hygroscopic (7% water) under the same conditions. The same situation pertains regarding the amorphous form.

What is claimed is:

1. The crystalline form of hydrated [1alpha,9alpha] 6,10-dioxo-N-(2-ethoxy-5-oxo-tetrahydro-3-furanyl)-9[[(1-isoquinolyl)carbonyl]amino]octahydro-6H-pyridazino[1,2-a][1,2]diazepin-1-carboxamide (form B) having Chemical Abstracts Registry No. 192755-52.

2. The crystalline form of hydrated [1alpha,9alpha] 6,10-dioxo-N-(2-ethoxy-5-oxo-tetrahydro-3-furanyl)-9[[(1-isoquinolyl)carbonyl]amino]octahydro-6H-pyridazino[1,2-a][1,2]diazepin-1-carboxamide (form B) according to claim 1, having at least one of the following characteristics:

a) Endothermal dehydration between 50 and 110° C. and between 110 and 130° C. and endothermal melting point from 162° C., b) infrared spectrum of form B having characteristic absorptions at approximately (nujol, $cm^{-1}$): 3569; 3447; 3322; 1778; 1682; 1660, c) XR diffraction pattern of form B having characteristic interlattice spacings equal to (d,Å): 11.34; 10.80; 10.06; 7.59; 7.16; 6.71; 6.41; 6.11; 5.44.

3. The crystalline form of hydrated [1alpha,9alpha] 6,10-dioxo-N-(2-ethoxy-5-oxo-tetrahydro-3-furanyl)-9[[(1-isoquinolyl)carbonyl]amino]octahydro-6H-pyridazino[1,2-a][1,2]diazepin-1-carboxamide (form B) as defined in claim 2, having characteristics a, b and c.

4. The crystalline form of hydrated [1alpha,9alpha] 6,10-dioxo-N-(2-ethoxy-5-oxo-tetrahydro-3-furanyl)-9[[(1-isoquinolyl)carbonyl]amino]octahydro-6H-pyridazino[1,2-a][1,2]diazepin-1-carboxamide (form B) as defined in claim 2, having an infrared spectrum substantially identical to that of FIG. 2B and an XR diffraction pattern substantially identical to that of FIG. 3B.

5. A composition to inhibit interleukin-1B conversion enzyme (ICE) comprising an inhibitorily effective amount of the compound of claim 1 and an inert, pharmaceutical carrier.

6. A process for the preparation of the form B of claim 1 comprising dissolving amorphous [1α-,9α]-6,10-dioxo-N-(2-ethoxy-5-oxo-tetrahydro-3-furanyl-9-[[(1-isoquinolylcarbonyl]-amino]-octahydro-6H-pyridazino[1,2-a][1,2]diazepin-1-carboxamide in an organic solvent at ambient temperature and subjecting the solution to crystallization to obtain form B.

7. The process of claim 6 wherein the solvent is toluene.

* * * * *